United States Patent [19]

Meiattini et al.

[11] 4,339,317

[45] Jul. 13, 1982

[54] DEVICE FOR PERFORMING MEASUREMENTS ON FLUIDS, DIRECTLY IN THE SAMPLE CONTAINER

[75] Inventors: Franco Meiattini, Siena; Giorgio Papeschi, Florence; Paolo Tarli, Monteriggioni; Paolo Neri, Siena, all of Italy

[73] Assignee: Instituto Sieroterapico e Vaccinogeno Toscano "Sclavo" S.p.A., Siena, Italy

[21] Appl. No.: 204,220

[22] Filed: Nov. 5, 1980

Related U.S. Application Data

[63] Continuation of Ser. No. 52,506, Jun. 27, 1979, abandoned.

[30] Foreign Application Priority Data

Jul. 5, 1978 [IT]  Italy ............................ 25351 A/78

[51] Int. Cl.³ ...................... G01N 27/28; G01N 27/30
[52] U.S. Cl. ................................................. 204/195 B
[58] Field of Search ....................... 204/195 R, 195 B

[56] References Cited

U.S. PATENT DOCUMENTS

| | | | |
|---|---|---|---|
| 2,886,771 | 5/1959 | Vincent | 204/195 R |
| 3,224,433 | 12/1965 | von Dalebor | 204/195 B |
| 3,497,442 | 2/1970 | Vincent | 204/195 R |
| 3,878,830 | 4/1975 | Bicher | 204/195 B |

*Primary Examiner*—T. Tufariello
*Attorney, Agent, or Firm*—Morgan, Finnegan, Pine, Foley & Lee

[57] ABSTRACT

For taking measurements on fluids, such as biological fluids (e.g. blood and the like), a device is disclosed which is a cylindrical body insertable in a syringe or a similar sampling container and has on the exposed face a set of electrodes or probes which are connected via appropriate electric leads to processing and displaying devices which permit the taking of immediate readings of important parameters such as pH, temperature, partial pressures of gases and so on.

10 Claims, 2 Drawing Figures

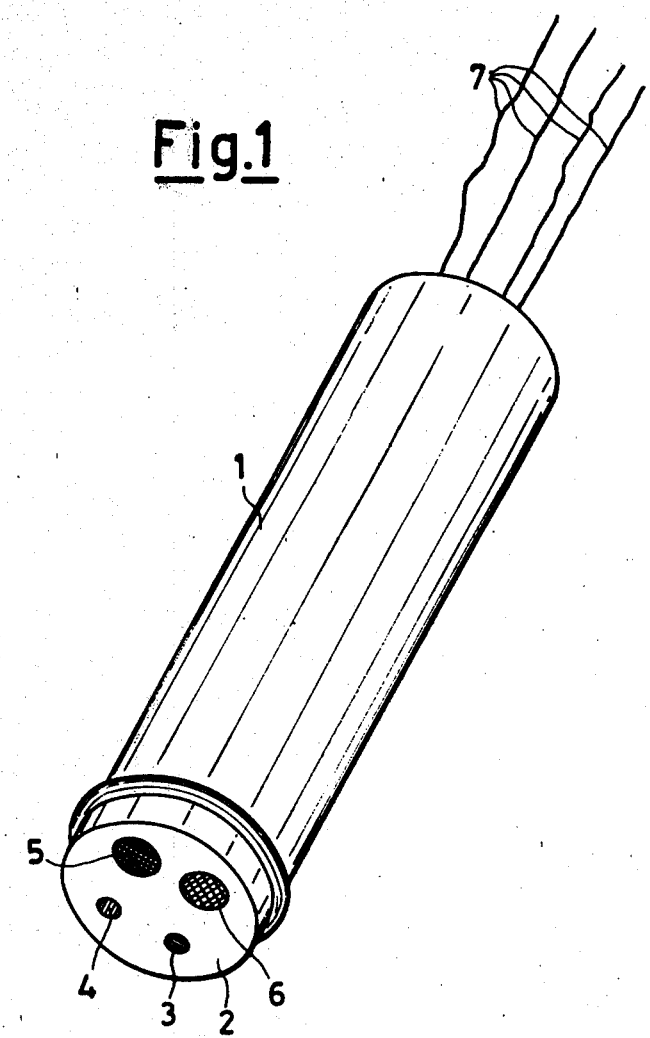

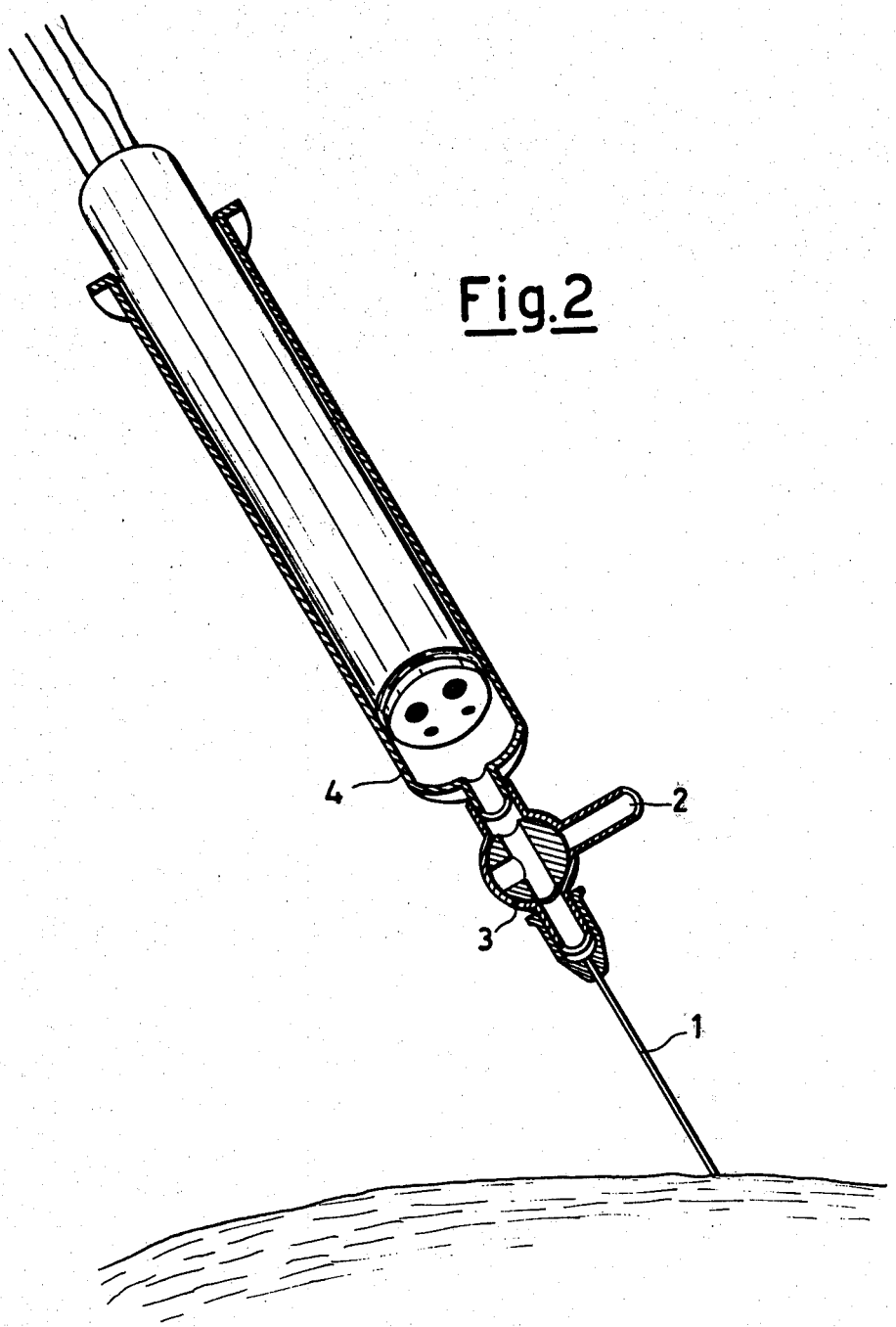

DEVICE FOR PERFORMING MEASUREMENTS ON FLUIDS, DIRECTLY IN THE SAMPLE CONTAINER

This is a continuation of application Ser. No. 052,506 filed June 27, 1979, now abandoned.

This invention relates to a device adapted to perform analytical check-up operations on samples of various origin.

A typical example is the check of the environmental pollution, which requires, as a rule, a special sensitivity and, concurrently, a simple performance of the analytical operations.

Another field of application is that of clinical tests in which there is the necessity of continuously monitoring the trend of certain analytical parameters, such as for example, during progress of certain surgical operations, or in reanimation centers.

The samples of the material to be analyzed must very often be transferred into specially provided containers for being sent to the analysis laboratory. The shortcomings which are generally experienced in such procedures are as follows:

increased occurrence of contamination and/or errors, such as sample-swapping, errors in copying down the sample identification codes and the like.
time waste
increased use up of laboratory vessels
a few particular cases, such as for example the case of analysis of gases in the blood, with attendant risk of alteration of the values of the substances to be measured, due to diffusion from and into the environment. This drawback is particularly significant in the case, mentioned above, of the operating rooms and the reanimation centers where, on the basis of the analytical results which are obtained, decisions of vital importance shall be taken.

It becomes thus imperative to be able to use a device which permits that these analysis may be performed, if and when possible, without transferring the samples and, preferably, at the very sampling spot.

The subject matter of this invention is a device which permits the taking of readings directly in the sampling container.

The device is composed, as shown in FIG. 1 of the accompanying drawings, which does not limit the invention, by a cylinder of an appropriate material 1, which is not prone to attack by the fluids to be analyzed and which can be sterilized if so required, appropriate sensors, 3, 4, 5 and 6 being inserted in said container so as to confront the side 2 of the cylinder which contacts the sample. The cylinder is so shaped as to be capable of acting like a piston in the hollow cylindrical space of the sampling container. The sensors are connected, via appropriate leads, to one or more detecting instrument(s) which serve for the processing and display of the readings.

FIG. 2 of the accompanying drawings offers an example of a piston of the kind referred to above, inserted in a hypodermic syringe for taking blood samples. In such a syringe (hypodermic) the sample of the blood which is drawn contacts, at very instant of sampling, the sensors housed in the head of the piston and which are specific for measurements of pH, $PO_2$, $PCO_2$ and temperature.

The sensors deliver their signals to the processing instruments which provide to process them and to display the readings on appropriate display screens and/or printed charts. By so doing, the results of the tests are made immediately available. The example given is by no means a limitation and does not exclude the use for different measurements and on samples other than those exemplified herein. An outstanding asset of the invention is that it becomes possible to effect the readings on reduced volumes of sample since it is by no way necessary to fill the cylindrical space completely, it being necessary and sufficient that the sensors projecting from the piston head are wetted. This fact also facilitates the performance of tests in a rapid sequential order by using a plural-way cock such as in FIG. 2.

As a matter of fact, once the hypodermic needle 1, has been inserted in the artery or the vein, the sample is drawn and, once the measurement has been taken, the sample itself can be discharged without removing the needle upon shifting the stream to the discharge 2 by the two-way cock 3 which is inserted between the needle and the body of the syringe 4. By rotating the cock handle again, the device is in readiness for the next sampling and so forth. In the case in which there is the necessity of introducing in the sample a clot-preventing agent such as heparin, the device can be equipped with a 3-way cock, one way being intended to draw the clot-preventing agent.

A model of the device has been embodied by way of example only by combining in a single piston-cylinder assembly of a plastics material, a microelectrode of iridium and iridium oxide for measuring the pH, a microelectrode for measuring $PCO_2$, a polagraphic-type microelectrode for measuring $PO_2$ and a thermosensitive probe for taking sample temperature readings. This model of pistons can be inserted in a syringe, the latter being possibly surrounded by a thermostatic liner.

As a rule, the electrodes used in the analysis of blood gases are based on the following operating principles:

$PCO_2$ electrode:

This is composed by an electrode which is normally made of glass and is responsive to the protonic activity, and is immersed in a solution of $NaHCO_3$ in contact with a membrane through which diffusion of $CO_2$ can take place. When the $CO_2$ which is diffused through the membrane is solubilized (I) in the solution held between the electrode surface and the membrane, it shifts the equilibrium (II) towards the right, the protonic activity being consequently increased:

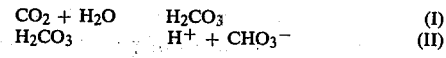

$$CO_2 + H_2O \rightleftharpoons H_2CO_3 \quad (I)$$
$$H_2CO_3 \rightleftharpoons H^+ + CHO_3^- \quad (II)$$

Under equilibrium conditions, the partial pressure of $CO_2$ will be the same on both faces of the membrane. Thus, variations of $PCO_2$ outside the membrane will originate equal variations of $PCO_2$ in the film of solution enclosed between the membrane and the electrode.

The potential of the glass electrode is measured relative to a reference electrode Ag/AgCl which finds the $Cl^-$ ions in the internal solution which contains also the bicarbonate (typical composition $NaHCO_3$: 0.05 M + NaCl: 0.1 M).

The cell is thus constituted as follows:

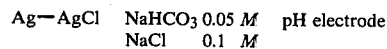

Ag—AgCl | $NaHCO_3$ 0.05 M | pH electrode
NaCl 0.1 M and its potential will be a function of the partial pressure of the $CO_2$ in the sample.

Therefore:

$$E = E'_o + 2.303 \frac{RT}{F} \log a_{H^+} = E''_o + 2.303 \frac{RT}{F} \log PCO_2$$

$PO_2$ electrode:

The $PO_2$ electrodes are of two types, viz.: galvanic or polarographic.

Galvanic electrodes are formed by two different metals which evolve, when immersed in an appropriate solution, a potential difference which is sufficient to reduce oxygen. The polarographic electrodes (Clark type), conversely, are composed by a platinum or a gold cathode which is biased to a potential value of from $-500$ mV and $-800$ mV relative to a reference electrode having saturated calomel.

A membrane, for example of Teflon (R.T.M.) separates the sample being tested from an internal solution which can be potassium chloride, or a pH 7 buffer. This solution must be present as a very thin layer between the membrane and the platinum cathode and must contain ions which fix the potential of the reference Ag/AgCl electrode. The oxygen diffused through the membrane is reduced to $OH^-$ on the cathode and the intensity of current which accompanies the reaction is proportional to the partial pressure of the oxygen in the sample.

pH electrodes:

The electrodes for measuring the protonic activity or pH are essentially glass membrane electrodes. This thin glass membrane separates the solution being tested from an internal buffer solution in which an Ag/AgCl electrode, or an $Hg/Hg_2Cl_2$ electrode is immersed. The potential of this element is measured relative to a reference half-cell and varies according to the relationship:

$$E = E'_o + 2.303 \frac{RT}{F} \log H^+ = E_o - 2.303 \frac{RT}{F} pH$$

The glass electrodes can take different shapes (capillary tube, planar or spherical head) but it is difficult to combine the small size with an adequate mechanical robustness, a low electric impedance and a high response velocity.

The electrodes described above, of the kind normally used in the measurements of pH, $PCO_2$ and $PO_2$ can permit that the present invention may be reduced to practice only if their physical dimensions permit the simultaneous insertion of such electrodes in the piston.

A nonlimiting example of embodiment of the invention is a piston comprising the following miniaturized sensors:

1. $Ir/IrO_2$ electrode for measuring the pH
2. $PCO_2$ electrode composed by an $Ir/IrO_2$ microelectrode surrounded by a Au and Pt guard of the diameter of 3 mm, immersed in an appropriate solution and coated by a $CO_2$-pervious membrane
3. Voltameter type microelectrode with a cathode of Pt (or Au) immersed in an appropriate solution and coated by an oxygen-previous membrane.

We claim:

1. A device for performing analytical measurements on body fluids, such as blood, comprising:
   a disposable syringe having opposing ends with a disposable needle at one end for drawing the body fluids within the syringe, and
   a reusable cylindrical body slidably insertable into and movable in said syringe from and through said other syringe end, wherein said body is shaped relative to the walls of the syringe between the ends thereof so as to act like a piston therein for withdrawing said body fluids, and wherein said body includes a plurality of sensors at the end thereof adjacent said needle for contacting body fluids drawn within said syringe, and means connected to said sensors and at the other end of said body for connection to instruments for detection and displaying data.

2. A device according to claim 1, wherein the needle end of said syringe includes a neck for connection to a plural-way cock.

3. A device according to claim 1, wherein the plurality of the sensors comprises an electrode for measuring the pH.

4. A device according to claim 1, wherein the plurality of the sensors comprises an electrode for measuring the $PCO_2$.

5. A device according to claim 1, wherein the plurality of the sensors comprises an electrode for measuring the $PO_2$.

6. A device according to claim 1, wherein the plurality of the sensors comprises an electrode for measuring the pCa.

7. A device according to claim 1, wherein the plurality of the sensors comprises an electrode for measuring the PCl.

8. A device according to claim 1, wherein the plurality of the sensors comprises an electrode for measuring the $pNO_3$.

9. A device according to claim 1, wherein the plurality of the sensors comprises a thermosensitive probe.

10. A device according to claim 1, equipped with a thermostatic control system.

* * * * *